United States Patent [19]

Metzner et al.

[11] Patent Number: 5,156,673

[45] Date of Patent: Oct. 20, 1992

[54] COMPOSITION FOR PRESERVATION OF WOOD AND WOOD-BASED MATERIALS

[75] Inventors: Wolfgang Metzner; Rainer Grüning, both of Krefeld, Fed. Rep. of Germany

[73] Assignee: Deutsche Solvay-Werke GmbH, Solingen, Fed. Rep. of Germany

[21] Appl. No.: 127,976

[22] Filed: Dec. 3, 1987

[30] Foreign Application Priority Data

Dec. 5, 1986 [DE] Fed. Rep. of Germany ....... 3641554

[51] Int. Cl.$^5$ ................................................. C09D 5/14
[52] U.S. Cl. .................. 106/15.05; 252/383; 252/384; 514/383
[58] Field of Search ................ 514/359, 383; 106/15.05; 252/383, 384

[56] References Cited

U.S. PATENT DOCUMENTS 4,542,146  9/1985  Van Gestel et al. ................ 514/383
4,661,382  4/1987  Cooke, Jr. .......................... 428/541

FOREIGN PATENT DOCUMENTS 2551560  4/1981  Fed. Rep. of Germany .

*Primary Examiner*—Amelia Burgess Yarbrough
*Attorney, Agent, or Firm*—Foley & Lardner

[57] ABSTRACT

A composition for preservation of wood or wood-based materials comprising 1-[[2-(2,4-dichlorophenyl)-1,3-dioxolan-2-yl]methyl]-1H-1,2,4-triazole, at least one of o,o-diethyl o-(3,5,6-trichloro-2-pyridyl) thiophosphate, o,o-diethyl o-(α-cyanobenzylidene-amino) thiophosphate, O-ethyl o-(2,4-dichlorophenyl)-S-n-propyl dithiophosphate and o,o-diethyl o-(1,6-dihydro-6-oxo-1-phenyl-3-pyridazinyl) thiophosphate, and a suspending agent comprised of at least one of a diluent, an emulsifier and a wetting agent, is provided, together with a process of preparing the composition by mixing the components thereof.

12 Claims, No Drawings

COMPOSITION FOR PRESERVATION OF WOOD AND WOOD-BASED MATERIALS

BACKGROUND OF THE INVENTION

The present invention relates to a composition to be used for preservation of wood and wood-based materials, wherein said composition comprises 1-[[2-(2,4-dichlorophenyl)-1,3-dioxolan-2-yl]methyl]-1H-1,2,4-triazole, (b) at least one compound selected from the group consisting of o,o-diethyl o-(3,5,6-trichloro-2-pyridyl) thiophosphate, o,o-diethyl o-(α-cyano-benzylidene-amino) thiophosphate, o-ethyl o-(2,4-dichlorophenyl)-S-n-propyl dithiophosphate and o,o-diethyl o-(1,6-dihydro-6-oxo-1-phenyl-3-pyridazinyl) thiophosphate and at least one diluent. Optionally, said composition further comprises at least one of the group consisting of another fungicide, a processing auxiliary, or additive, an organic chemical binding agent, a fixative, a dye, and a pigment. The present invention also relates to a process for preparation of the above-described composition for preservation of wood and wood-based materials.

The chemical compound, 1-[[2-(2,4-dichloro-phenyl)-1,3-dioxolan-2-yl]-methyl]-1H-1,2,4-triazole ("azaconazole"), having the structural formula

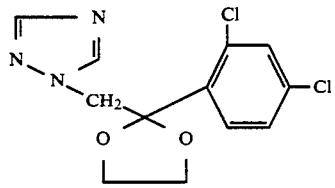

is known, and has been described in German Patent No. 2,551,560 as a fungicidal and plant growth regulatory agent for agricultural use. It is not known, however, whether azaconazole can be used as a wood preservative.

Demands placed on a good wood preservative are considerably more than those placed on a fungicide used for plant protection. A fungicide need only be active against fungi, but a good wood preservative has to be active not only against wood-discoloring and wood-destroying fungi, but wood-damaging insects as well, particularly termites. Furthermore, a wood preservative, but not a fungicide, has to exhibit a good long-term activity.

Coincidentally, esters of thiophosphoric acid are known to exhibit good insecticidal action and have been employed in protection of plants against insects. But it is not known, however, whether these insecticides can also be used as wood preservatives. In general, a good insecticide for purposes of plant protection, by definition, is not a good wood preservative. This is because a good insecticide must be degraded after a certain period of time, thus eliminating the possibility of contamination of the food chain and endangering the health of humans and animals. Moreover, a good insecticide must not penetrate too deeply into parts of plants upon application, in order that it can be easily washed off. In contrast, long-term activity and good penetrating ability are necessary characteristics in preservatives for wood and wood-based material. For purposes of the present invention, a wood-based material is a material made from wood, such as plywood, pressed wood, particleboard and wood laminates.

It is also not known whether a combination of fungicide and insecticide can be used as a wood preservative, without one of them impairing the activity of the other. Even if these fungicides and insecticides, hereinafter collectively referred to as "biocides", can be used in combination as a wood preservative, it is not known what amount of each is necessary to produce an optimum product.

SUMMARY OF THE INVENTION

It is therefore, an object of the present invention to provide a composition for preservation of wood and wood-based materials, otherwise referred to as a wood preservative, that is highly active against wood-discoloring and wood-destroying fungi, and against wood-damaging insects, particularly termites.

It is another object of the present invention to provide a wood preservative which has long-term fungicidal and insecticidal activities.

It is still another object of the present invention to provide a wood preservative that has good penetrating ability in wood and wood-based materials.

It is yet another object of the present invention to provide a wood preservative in which the fungicidal action is not impaired by presence of an insecticide, and vice versa.

It is a further object of the present invention to provide a process for preparing a wood preservative that possesses the above-described properties.

In accomplishing these and other objects of the present invention, there has been provided a composition for preservation of wood and wood-based materials comprising a predetermined amount of components (a) a compound, 1-[[2-(2,4-dichlorophenyl)-1,3-dioxolan-2-yl]methyl]-1H-1,2,4-triazole, (b) at least one compound selected from the group consisting of o,o-diethyl o-(3,5,6-trichloro-2-pyridyl) thiophosphate, o,o-diethyl o-(α-cyano-benzylidene-amino) thiophosphate, o-ethyl o-(2,4-dichlorophenyl)-S-n-propyl dithiophosphate and o,o-diethyl o-(1,6-dihydro-6-oxo-1-phenyl-3-pyridazinyl) thiophosphate, and (c) a suspending agent that comprises at least one of a diluent, an emulsifier and a wetting agent.

In accordance with another aspect of the present invention, there has been provided a composition as described above, wherein amounts of components (a)-(c) are present in a mixture with an amount of at least one of components (d) an organic binding agent, (e) a fixative, and (f) a plasticizer.

In accordance with yet another aspect of the present invention, there has been provided a composition as described above, wherein said composition further comprises a predetermined amount of components (g) at least one other biocide soluble in said diluent, and (h) at least one of a water-soluble or water-insoluble dye, color pigment, anti-corrosive agent, siccative and UV-stabilizer.

In accordance with still another aspect of the present invention, there has been provided a composition as described above, wherein said composition further comprises a fungicide which is soluble in component (c).

In accordance with a further aspect of the present invention, there has been provided a process for preparation of a wood and wood-based preservative comprising the step of mixing the necessary components, for example (a)-(c) and at least one of components (d), (e) and (f), as described above.

DETAILED DESCRIPTION OF THE PREFERRED EMBODIMENTS

It has been discovered that objects of the present invention can be attained by the present invention, a composition for preservation of wood and wood-based materials, comprising a predetermined amount of each of components (a) 1-[[2-(2,4-dichlorophenyl)-1,3-dioxolan-2-yl]methyl]-1H-1,2,4-triazole, (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichlorophenyl)-S-n-propyl dithiophosphate and o,o-diethyl o-(1,6-dihydro-6-oxo-1-phenyl-3-pyridazinyl) thiophosphate, and (c) a suspending agent comprising at least one of the group consisting of a diluent, an emulsifier, and a wetting agent.

This composition can be in the form of a concentrate to be suitably diluted with a diluent prior to use, or can be in a ready-to-use form, to be used directly without dilution. Furthermore, the components of this composition can be present in the form of a kit or package, to be mixed by a user prior to use. Optionally, the composition further comprises at least one compound selected from the group consisting of another fungicide, a processing auxiliary, or additive, an organic chemical binding agent, a fixative, a dye, and a pigment.

In one preferred embodiment, the composition comprises 0.001%-5% by weight, preferably 0.2%-2% by weight, of (a) 1-[[2-(2,4-dichlorophenyl)-1,3-dioxolan-2-yl]methyl]-1H-1,2,4-triazole, 0.3%-3% by weight, preferably 0.5%-2% by weight, of (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichloro-phenyl)-S-n-propyl dithiophosphate and o,o-diethyl o-(1,6- dihydro-6-oxo-1-phenyl-3-pyridazinyl) thiophosphate and more than 75% by weight, preferably more than 90% by weight of (c) a suspending agent that comprises at least one of a diluent, an emulsifier and a wetting agent.

The diluent of component (c) within the context of the present invention comprises an organic chemical solvent or solvent mixture, preferably at least one polar, organic chemical solvent and/or an oily or oil-like low-volatility organic chemical solvent, or a mixture of water and/or at least one organic chemical solvent, preferably at least one polar organic chemical solvent and/or an oily or oil-like, low-volatility, organic chemical solvent or solvent mixture, and at least one emulsifier and/or wetting agent.

In another embodiment of the present invention, the composition further comprises at least one of components (d) a binding agent and/or (e) a fixative, in a total amount of 0.1%-25% by weight, preferably 1%-18% by weight, based on total weight of solids.

In still another embodiment of the present invention, a weight ratio of components (d) and/or (e), i.e., of the present binding agent and/or, fixative, to component (c), the diluent or diluent mixture and to an emulsifier or emulsifier mixture and/or wetting agent or wetting agent mixture contained in the agent is 8.5:1 to 1:99.

In yet another embodiment of the present invention, the organic chemical binding agent, or binding agent mixture, can be partly replaced by at least one plasticizer.

In a preferred embodiment of the present invention, the composition comprises 0.001%-5% by weight, preferably 0.2%-2% by weight, of (a) 1-[[2-(2,4-dichlorophenyl)-1,3-dioxolan-2-yl]methyl]-1H-1,2,4-triazole, 0.3%-3% by weight, preferably 0.5%-2% by weight, of (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichlorophenyl)-S-n-propyl dithio-phosphate and o,o-diethyl o-(1,6-dihydro-6-oxo-1-phenyl-3-pyridazinyl) thiophosphate and 0.1%-28% by weight, preferably 1%-18% by weight, based on total weight of solids, of at least one of (d) an organic chemical binding agent and (e) a fixative, or (f) a plasticizer, and the weight ratio of the total content of (d) an organic chemical binding agent and/or (e) a fixative or (f) a plasticizer to the total content of (c) a diluent (including solvent or solvent mixture and/or water and/or emulsifier and/or wetting agent) is 1:1.2 to 1:99, preferably 1:2 to 1:25.

In another embodiment of the present invention, the diluent preferably comprises at least one organic chemical, low-volatility solvent having an evaporation number above 35 and a flash point above 30° C., preferably of an oily or oil-like, organic chemical solvent or solvent mixture or contains one or more of these low-volatility solvents.

In accordance with a further embodiment of the present invention, 0.5% to 23% by weight, preferably 2%-15% by weight, of the organic chemical, low-volatile solvent or solvent mixture having a flash point above 30° C. can be replaced by an equivalent amount of one or more organic chemical binding agents and/or fixatives, the organic chemical binding agents and/or fixatives employed being those which are in the solvent or solvent mixture dispersible or emulsifiable, but preferably soluble, and the replacement being subject to the provision that the mixture obtained or solvent mixture obtained also exhibits a flash point above 30° C., and the organic chemical solvent or solvent mixture is an oily or oil-like solvent.

In accordance with a preferred embodiment of the present invention, a ready-to-use agent for the preservation of wood and wood-based materials comprises a mixture of 0.001%-5% by weight, preferably 0.2%-2% by weight, of (a) 1-[[2-(2,4-dichlorophenyl)-1,3-dioxolan-2-yl]methyl]-1H-1,2,4-triazole, 0.3%-3% by weight, preferably 0.5%-2% by weight, of (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichlorophenyl)-S-n-propyl dithiophosphate and o,o-diethyl o-(1,6-dihydro-6-oxo-1-phenyl-3-pyridazinyl) thiophosphate, 0.1%-28% by weight, preferably 1%-18% by weight, of at least one of (d) an organic chemical binding agent and (e) a fixative, or (f), plasticizer, 0%-5% by weight, preferably 0.01%-4% by weight, of (g) at least one other biocide or biocide mixture soluble in the organic chemical solvent or solvent mixture, 0%-8% by weight, preferably 0.1%-4% by weight, of (h) at least one of a water-soluble and/or water-insoluble dye, color pigment and/or anti-corrosive agent, siccative and/or UV-stabilizer and 99.599% by weight to 51% by weight, preferably 98.19% by weight to 70% by weight, of (c) a diluent or diluent mixture comprising at least one organic chemical solvent or solvent mixture and/or water and/or at least one emulsifier and/or wetting agent or mixture thereof.

In accordance with another embodiment of the present invention, the composition comprises 0.001%–5% by weight, preferably 0.2%–2% by weight, of (a) 1-[[2-(2,4-dichlorophenyl)-1,3-dioxolan-2-yl]methyl]-1H-1,2,4-triazole, 0.3%–3% by weight, preferably 0.5%–2% by weight, of (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichlorophenyl)-S-n-propyl dithiophosphate and o,o-diethyl o-(1,6-dihydro-6-oxo-1-phenyl-3-pyridazinyl) thiophosphate, 2%–85% by weight, preferably 8%–40% by weight, based on total weight of solids, of at least one of (d) an organic chemical binding agent and (e) a fixative, or (f) a plasticizer, and a weight ratio of total content of organic chemical binding agent and/or fixative or plasticizer to the total content of diluent (including solvent or solvent mixture and/or water and/or emulsifier and/or wetting agent) is 8.5:1 to 1:48, preferably 1:1.45 to 1:11.5.

In accordance with a preferred embodiment of the present invention, the composition for preservation of wood and wood-based materials comprises 0.001%–5% by weight, preferably 0.2%–2% by weight, of (a) 1-[[2-(2,4-dichloro-phenyl)-1,3-dioxolan-2-yl]methyl]-1H-1,2,4-triazole, 0.3%–3% by weight, preferably 0.5%–2% by weight, of (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichloro-phenyl)-S-n-propyl dithiophosphate and o,o-diethyl o-(1,6-dihydro-6-oxo-1-phenyl-3-pyridazinyl) thiophosphate, 2%–85% by weight, preferably 8%–60% by weight, of at least one of (d) an organic chemical binding agent and (e) a fixative, or (f) a plasticizer, 20%–0% by weight, preferably 8%–1% by weight, of a fungicide or fungicide mixture soluble in the organic chemical solvent or solvent mixture and a diluent or diluent mixture as the remaining component, comprising at least one organic chemical solvent or solvent mixture or water and/or solvent or solvent mixture and/or at least one emulsifier and/or wetting agent or a mixture thereof and also, optionally a dye, a color pigment, an anticorrosive agent, a siccative and a UV-stabilizer.

In another embodiment of the present invention, a composition can be prepared by a process of mixing components (a) 1-[[2-(2,4-dichlorophenyl)-1,3-dioxolan-2-yl]methyl]-1H-1,2,4-triazole, (b) at least one compound selected from the group consisting of o,o-diethyl o-(3,5,6-trichloro-2-pyridyl) thiophosphate, o,o-diethyl o-(α-cyanobenzylidene-amino) thiophosphate, o-ethyl o-(2,4-dichloro-phenyl)-S-n-propyl dithiophosphate and o,o-diethyl o-(1,6-dihydro-6-oxo-1-phenyl-3-pyridazinyl) thiophosphate, and (c) a suspending agent that comprises at least one of a diluent, an emulsifier and a wetting agent at temperatures of −5° C. to 80° C., preferably 15° C. to 45° C., and at pressures of 400 mm Hg to 850 mm Hg (0.5332 to 1.1332 bar), preferably 600 mm Hg to 790 mm Hg (0.7999 to 1.0532 bar). Optionally at least one of the components (d)–(h) and one other fungicide, as described above, can be added.

EXAMPLE 1

A termiticidal and fungicidal wood preservative of the following composition was made, particularly for impregnation:

| | |
|---|---|
| 1-[[2-(2,4-dichlorophenyl)-1,3-dioxolan-2-yl]methyl]-1H-1,2,4-triazole (azaconazole) | 1.0% |
| o,o diethyl o-(α-cyanobenzylidene-amino) thiophosphate (phoxim) | 1.5% |
| dibutyl phthalate | 6.0% |
| monitor dye | 0.2% |
| perfume | 0.04% |
| white spirit (mixture of aliphatic and aromatic hydrocarbons) | 91.26% |

EXAMPLE 2

A termiticidal and fungicidal wood preservative of the following composition was made, particularly for impregnation:

| | |
|---|---|
| 1-[[2-(2,4-dichlorophenyl)-1,3-dioxolan-2-yl]methyl]-1H-1,2,4-triazole (azaconazole) | 1.4% |
| o,o-diethyl o-(3,5,6-trichloro-2-pyridyl) thiophosphate (chlorpyrifos) | 1.2% |
| dibutyl phthalate | 4.0% |
| gas oil (high boiling) | 10.0% |
| mineral oil (mixture of aliphatic and aromatic hydrocarbons) | 83.40% |

EXAMPLE 3

A termiticidal and fungicidal wood preservative of the following composition was made:

| | |
|---|---|
| 1-[[2-(2,4-dichlorophenyl)-1,3-dioxolan-2-yl]methyl]-1H-1,2,4-triazole (azaconazole) | 0.08% |
| o,o-diethyl o-(1,6-dihydro-6-oxo-1-phenyl-3-pyridazinyl) thiophosphate (pyridafenthion) | 1.4% |
| boiled linseed oil | 4.0% |
| mineral oil (mixture of aliphatic and aromatic hydrocarbons) | 93.80% |

EXAMPLE 4

A termiticidal and fungicidal wood preservative of the following compositions was made:

| | |
|---|---|
| 1-[[2-(2,4-dichlorophenyl)-1,3-dioxolan-2-yl]methyl]-1H-1,2,4-triazole (azaconacole) | 0.37% |
| o,o-diethyl o-(α-cyanobenzylidene-amino) thiophosphate (phoxim) | 0.9% |
| 2-isopropoxyphenyl-N-methylcarbamate (propoxur) | 0.9% |
| dibutyl phthalate | 4.0% |
| bitumen | 1.0% |
| perfume | 0.042% |
| white spirit (mixture of aliphatic and aromatic hydrocarbons) | 92.788% |

EXAMPLE 5

A termiticidal and fungicidal wood preservative of the following composition was made:

| | |
|---|---|
| 1-[[2-(2,4-dichlorophenyl)-1,3-dioxolan-2-yl]methyl]-1H-1,2,4-triazole (azaconacole) | 1.4% |
| o,o-diethyl o-(α-cyanobenzylidene-amino) | 1.6% |

-continued

| | |
|---|---|
| thiophosphate (phoxim) | |
| 2-isopropoxyphenyl-N-methylcarbamate (propoxur) | 0.9% |
| ethylglycol acetate | 3.0% |
| boiled linseed oil | 5.0% |
| spindle oil | 10.0% |
| perfume | 0.04% |
| white spirit (mixture of aliphatic and aromatic hydrocarbons) | 78.16% |

EXAMPLE 6

A termiticidal and fungicidal wood preservative of the following composition was made:

| | |
|---|---|
| 1-[[2-(2,4-dichlorophenyl)-1,3-dioxolan-2-yl]methyl]-1H-1,2,4-triazole (azaconacole | 1% |
| o,o-diethyl o-(α-cyanobenzylidene-amino) thiophosphate (phoxim) | 1% |
| 2-isopropoxyphenyl-N-methylcarbamate (propoxur) | 1% |
| 2-sec.-butylphenyl-N-methylcarbamate (Baycarb) | 1% |
| 70% alkyd resin | 4% |
| white spirit (mixture of aliphatic and aromatic hydrocarbons) | 92% |

What is claimed is:

1. A composition for preservation of wood or wood-based materials consisting essentially of, in admixture:
   (a) from about 0.001% to 5%, based on the total weight of all components, of 1-[[2-(2,4-dichloro-phenyl)-1,3-dioxolan-2-yl]methyl]-1H-1,2,4-triazole,
   (b) from about 0.3% to 3%, based on the total weight of all components, of at least one compound selected from the group consisting of o,o-diethyl o-(3,5,6-trichloro-2-pyridyl) thiophosphate, o,o-diethyl o-(a-cyano-benzylidene-amino) thiophosphate, o-ethyl o-(2,4-dichloro-phenyl)-S-n-propyl dithiophosphate and o,o-diethyl o-(1,6-dihydro-6-oxo-1-phenyl-3-pyridazinyl) thiophosphate, and
   (c) a suspending agent selected from the group consisting of a diluent, an emulsifier, a wetting agent, and mixtures thereof.

2. A composition as claimed in claim 1, wherein the amount of component (a) is from about 0.2% to 2%, and the amount of component (b) is from about 0.5% to 2% of total weight of all components.

3. A composition as claimed in claim 1, wherein said suspending agent is more than 75% of total weight of all components.

4. A composition as claimed in claim 1, wherein said diluent is at least one of an organic solvent and water, and said organic solvent comprises at least one of a polar solvent and an oily or oil-like low-volatility organic solvent.

5. A composition as claimed in claim 4, wherein said low-volatility solvent that has an evaporation number above 35 and a flash point above 30° C.

6. A composition as claimed in claim 1, wherein said composition further consists essentially of an amount of one other fungicide which is soluble in component (c).

7. A composition for preservation of wood or wood-based materials consisting essentially of, in admixture:
   (a) from about 0.001% to 5%, based on the total weight of all components, of 1-[[2-(2,4-dichloro-phenyl)-1,3-dioxolan-2-yl]methyl]-1H-1,2,4-triazole,
   (b) from about 0.3% to 3%, based on the total weight of all components, of at least one compound selected from the group consisting of o,o-diethyl o-(3,5,6-trichloro-2-pyridyl) thiophosphate, o,o-diethyl o-(a-cyano-benzylidene-amino) thiophosphate, o-ethyl o-(2,4-dichloro-phenyl)-S-n-propyl dithiophosphate and o,o-diethyl o-(1,6-dihydro-6-oxo-1-phenyl-3-pyridazinyl) thiophosphate, and
   (c) at least 75%, based on the total weight of all components, of a suspending agent that includes at least one of a diluent, an emulsifier and a wetting agent.

8. A composition as claimed in claim 1, wherein component (b) is o,o-diethyl o-(a-cyano-benzylidene-amino) thiophosphate.

9. A composition as claimed in claim 1, wherein component (b) is o-ethyl o-(2,4-dichloro-phenyl)-S-n-propyl dithiophosphate.

10. A composition as claimed in claim 1, wherein component (b) is o,o-diethyl o,(1,6-dihydro-6-oxo-1-phenyl-3-pyridazinyl) thiophosphate.

11. A composition as claimed in claim 1, consisting essentially of component (a), component (b), an oily, low-volatility, organic solvent, and at least one of an emulsifier and a wetting agent.

12. A composition as claimed in claim 1, consisting essentially of component (a), component (b), and an oily, low-volatility, organic solvent.

* * * * *